(12) United States Patent
Strecker

(10) Patent No.: US 6,602,286 B1
(45) Date of Patent: Aug. 5, 2003

(54) IMPLANTABLE VALVE SYSTEM

(76) Inventor: Ernst Peter Strecker, Vierordt Str 7A, 76228 Karlsruhe (DE)

(*) Notice: Subject to any disclaimer, the term of this patent is extended or adjusted under 35 U.S.C. 154(b) by 3 days.

(21) Appl. No.: 09/697,094

(22) Filed: Oct. 26, 2000

(51) Int. Cl.[7] .................................................. A61F 2/06
(52) U.S. Cl. ...................................................... 623/1.24
(58) Field of Search .............................. 623/1.24, 1.26, 623/2.1, 2.12, 2.14, 2.13, 2.25

(56) References Cited

U.S. PATENT DOCUMENTS

| | | | |
|---|---|---|---|
| 4,851,001 A | | 7/1989 | Taheri ............................ 623/2 |
| 4,872,874 A | | 10/1989 | Taheri ............................ 623/1 |
| 4,935,030 A | * | 6/1990 | Alonso ........................ 623/2.1 |
| 5,002,567 A | * | 3/1991 | Bona et al. .................... 623/2.1 |
| 5,147,389 A | | 9/1992 | Lane .............................. 623/2 |
| 5,219,355 A | | 6/1993 | Parodi et al. ................ 606/191 |
| 5,254,127 A | | 10/1993 | Wholey et al. .............. 606/153 |
| 5,358,518 A | * | 10/1994 | Camilli ........................ 623/2.1 |
| 5,500,014 A | | 3/1996 | Quijano et al. |
| 5,643,208 A | | 7/1997 | Parodi .......................... 604/96 |
| 5,693,087 A | | 12/1997 | Parodi ............................ 623/1 |
| 5,810,847 A | | 9/1998 | Laufer et al. ................ 606/142 |
| 5,879,320 A | | 3/1999 | Cazenave ........................ 604/8 |
| 5,895,419 A | * | 4/1999 | Tweden et al. .............. 623/2.1 |
| 6,139,575 A | * | 10/2000 | Shu et al. .................... 623/2.12 |
| 6,287,334 B1 | * | 9/2001 | Moll et al. .................. 623/1.24 |
| 6,299,637 B1 | * | 10/2001 | Shaolian et al. ........... 623/1.24 |
| 6,440,164 B1 | * | 8/2002 | DiMatteo et al. .......... 623/1.24 |

FOREIGN PATENT DOCUMENTS

| | | |
|---|---|---|
| EP | 0 380 666 B1 | 12/1993 |
| EP | 0 466 518 B1 | 2/1996 |
| FR | 2 728 457 | 6/1996 |
| WO | WO 88/00459 | 1/1988 |
| WO | WO 90/15582 | 12/1990 |
| WO | WO 95/01669 | 1/1995 |
| WO | WO 96/19159 | 6/1996 |
| WO | WO 98/03656 | 1/1998 |
| WO | WO 98/46115 | 10/1998 |
| WO | WO 98/57599 | 12/1998 |
| WO | WO 99/04724 | 2/1999 |
| WO | WO 00/67679 | 11/2000 |
| WO | WO 01/17462 | 3/2001 |
| WO | WO 01/156500 | 8/2001 |

OTHER PUBLICATIONS

Love, Jack W., Cardiac Prostheses, In *Principles of Tissue Engineering*, Lanza et al. eds. (Academic Press) Ch. 34, pp. 455–467 (2000).

* cited by examiner

Primary Examiner—Corrine McDermott
Assistant Examiner—Suzette J. Jackson
(74) Attorney, Agent, or Firm—RatnerPrestia

(57) ABSTRACT

An implantable valve having a valve element or leaflet and a base that is attachable to a vessel wall using a connector such as a screw, pin or a staple. The valve can be implanted using a catheter to position the valve in a desired location and drive the connector into the vessel wall. The valve can be used as a venous valve to control blood flow within the veins, arteries, heart or the aorta of a patient.

42 Claims, 16 Drawing Sheets

IMPLANTABLE VALVE SYSTEM

BACKGROUND OF THE INVENTION

Venous valves can improve the severe symptoms of patients with post thrombotic syndrome suffering from swelling and ulcerations of their legs. This condition can be caused by stenosis and occlusions of the veins and deterioration of the venous valves. Certain techniques have been developed to surgically restore incompetent valves or to implant devices that aid in such restoration. However, there remain many situations in which a valve is compromised to the extent that these options are not effective and valve replacement must be considered. By replacement of the venous valves, the capillary venous pressure can be decreased in this group of patients eventually improving their condition.

Venous valves have been proposed that consist of a stent device combined with a moving valve being mounted to the stent. However, stents can reduce the effective orifice area of the valve which increases the transvalvular pressure gradient. A further drawback to this valve is that a stent has fixed dimensions and remains in contact with the total circumference of the inner venous surface which, therefore, can irritate a large amount of the venous wall, especially the endothelium. This can be followed by intimal hyperplasia and thrombosis. Further, trauma to the wall of the vein is induced by shear stress between the wall components and the stent, because the venous diameter changes normally. The failure to accommodate growth of the patient is particularly problematic for children undergoing valve replacement, for example. A continuing need exists, therefore, for improvements in valve replacement systems and in methods for placement of such valves.

SUMMARY OF THE INVENTION

The present device relates to an implantable valve having a valve element that is attached to region of the a vessel wall with a tissue connector. The valve can be placed within a body lumen using endoluminal techniques such as a percutaneous catheter. The valve element can be formed with a biocompatible material such as plastic (e.g., PTFE) with a generally oval or circular shape. Materials such as textile fabric and donor tissue, such as fascia lata, for example, can also form the valve element. The valve element rotates relative to a position on the vessel wall where the connector is located and moves between open and closed positions to permit fluid flow in one direction and prevent fluid flow in the opposite direction.

The valve element can have a curved surface, with the generally convex side of the valve element facing against the preferential direction of flow of fluid within the lumen in which the valve is placed. The opposite side of the valve element can consequently have a concave shape. A preferred embodiment of the valve element uses a frame to reinforce the element. The periphery is preferably soft, however, to prevent vessel wall damage. The valve element generally has a diameter in a range between 2 mm and 45 mm, and a thickness between 0.2 mm and 3.0 mm.

The valve element or leaflet is attached to a stationary base such that the leaflet can move or rotate relative to the base. The base is attached to the vessel wall with a connector such as a pin, a screw, a staple, and/or an adhesive. In the event that open implantation is performed, a surgical suture can also be used as the connector. The connector can be used to attach the valve element to the base. In a preferred embodiment the base and the valve element can be formed as a unitary structure in which the valve element has a hinge region to provide for rotation of the valve element relative to the base.

A preferred embodiment of the invention uses a catheter to position the valve at a site within a body lumen and to attach the valve to a point on a wall of the lumen. The catheter can employ a system that attaches the valve to the vessel wall in which the catheter has a driver at the distal end that attaches the connector to the lumen wall. The catheter can have a guide that is used to position the distal end of the catheter, the guide and/or the connector for proper anchoring of the valve to the lumen. The guide can be a cord that extends through another catheter lumen or a sheath around the catheter that is connected at one end to the distal end of the catheter such that the user can mechanically pull the cord to bend the distal end of the catheter and consequently move the connector from one side of the lumen to the opposite side so that the portion of the connector that is to penetrate the vessel wall is properly oriented so as to be driven and securely attached. A release mechanism to detach the system from the valve and/or connector after placement can also be used.

Alternately, the valve can have a base with a connector to attach the valve to a lumen wall and a tubular wall connected to the base. The tubular wall has a proximal end with a proximal opening and a distal end with a distal opening. When implanted into a lumen, flow from the distal end to the proximal end forces the tubular wall into an open position thereby allowing flow through the tube while flow from the proximal end to the distal end forces the tubular wall into a closed position, thereby preventing flow in this direction. The valve can be shaped as a wedge shaped tube or as a curve shaped tube. The curve shaped tube can include a crease portion which allows the tube to collapse in the presence of back flow, thereby preventing back flow from entering the tube. The valve can be made from a silicone material.

The valve can also have a base with a connector to attach the valve to a lumen wall, a leaflet and a hinge connecting the base and the leaflet. The leaf or leaflet can be formed with an oval shape. The leaflet can have a concave shape. The leaflet can also have a rim and a center portion wherein the rim is thinner than the center portion. The valve includes a reinforcement frame which can be a metal filament. The valve can include a fabric material connecting the leaflet and the base. The fabric material can include a first layer and a second layer. A reinforcement member can be located between the first layer and the second layer.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
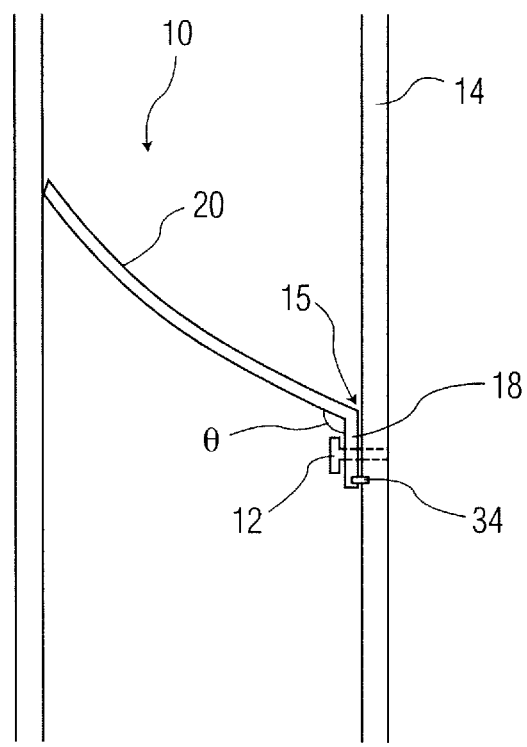
FIG. 1 illustrates a cross sectional view of a valve mounted within a vessel and attached to the vessel wall.

FIG. 1 illustrates a valve, identified generally as 10. In a preferred embodiment, the valve 10 is a venous valve for placement within a vein. The valve 10 can include a valve element 20 and a base 18, where the valve element or leaflet 20 is connected to the base 18 by a movable joint such as a hinge 15.

The valve 10 can be attached within a vessel having a vessel wall 14. The valve 10 can be attached to the vessel wall 14 by a tissue connector 12 which can include a pin, a screw or a staple, for example. The connector 12 can connect the valve 10 by its base 18 to the vessel wall 14. When the connector 12 is placed into the vessel wall 14, only a small portion of the connector 12 contacts the endothelium of the vessel wall 14 and the blood within the vessel. With such a configuration of the connector 12, there is less trauma to the wall 14 compared to the use of a stent, for example.

The valve 10 can also include a second connector 34. The second connector 34 can also attach the valve 10 to the vessel wall 14 through the base 18. The second connector 34, however, acts to stabilize the valve 10 and prevent twisting or turning of the valve 10 within the vessel when subjected to varying to fluid flow pressure.

Figure 2:
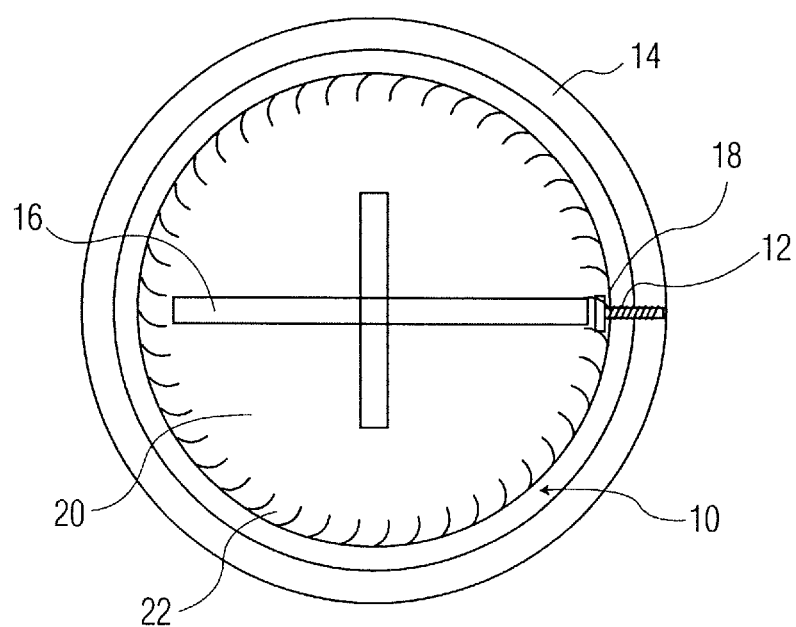
FIG. 2 shows a top view of a valve mounted within a vessel.

FIG. 2 illustrates a top view of the valve 10 attached to the vessel wall 14. The valve 10 can be made from a non-thrombogenic matter such as a plastic material (eg. PTFE or silicone), or other biocompatible materials. Other materials can also be used such as textile fabric or tissue from the patient. Material such as fascia lata, or pericardium can be taken from donors, as cadavers or from animals like pigs or can be produced by tissue engineering procedures. Fibroblast and endothelial cell cultures derived from human, bovine, and ovine sources can be seeded on biodegradable (glycolic acid) meshes can create valve leaflets. Xenograft leaflets can be made of human fibroblasts and bovine endothelial cells, and allograft leaflets can be made of bovine cells engineered in vitro. The leaflet 20 of the valve 10 can include at least one valve reinforcement frame 16. The valve frame 16 can help to prevent collapse of the valve 10 and increases the strength of the leaflet 20. The valve 10 can also include a rim 22. Preferably, the rim 22 of the leaflet 20 is formed of a compliant material to prevent damage to the vessel wall 14 during valve 10 motion and to form a tight junction between the wall 14 and valve 10 when the valve 10 is in a closed position.

A valve 10 having a compliant rim 22 allows physiological changing of the vessel wall 14 diameter without the valve 10 losing its function. The use of the valve 10 having a compliant rim 22 within a vessel can therefore offer a benefit over the use of a stent within the vessel. As the diameter of the vessel changes, the valve 10 can accommodate alteration of the vessel diameter within a certain range, thereby maintaining its function. The material of the leaflet and the rim 22 can fold around the valve frame 16 to accommodate the inner lumen of the vessel wall 14 when the valve 10 is in an opened state. The folding of this material and the rim 22 can accommodate different vessel diameters. Conversely, a stent in contact with the total circumference of the vessel wall during changes in the diameter of the vessel can cause stress on the wall surface. The valve element has a substantially oval shape with a diameter along the longitudinal axis that is preferably in the range between 2 mm and 2.5 cm. For certain applications the valve element can have a diameter of up to 45 mm. Such a valve element can be used in the heart. The thickness of the valve element is preferably between 0.2 mm and 3 mm.

Figure 3A:
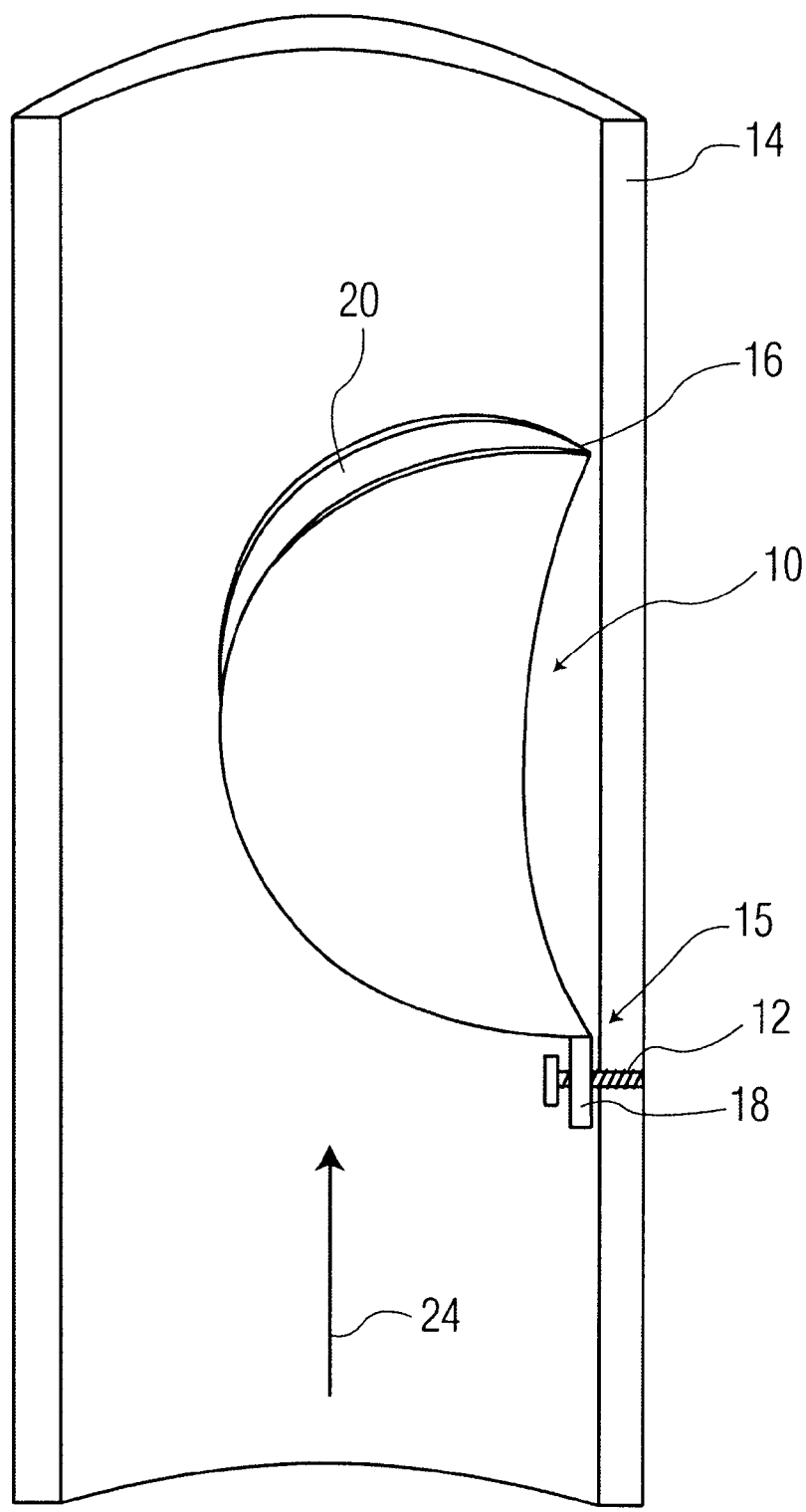
FIGS. 3A and 3B illustrate partial perspective and top view of the valve of FIG. 1 in an open position.
Figure 3B:
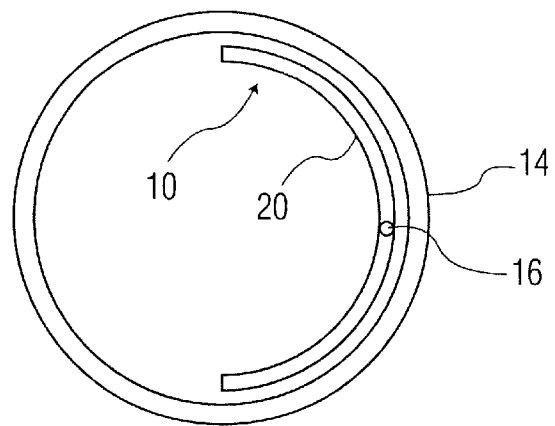

FIGS. 3A and 3B show the valve 10 in an open position. Fluid flow 24 past the valve 10 can cause the leaflet 20 of the valve 10 to rotate about or flex on its hinge 15. The hinge 15 connects the leaflet 20 to the base 18 and provides flexibility between the components 18, 20. The stiffness of the hinge 15 can be chosen such that flow of the fluid 24 past the valve 10 within the vessel can force the valve 10 to open. When flow has ceased, the valve 10 can return to a closed position.

FIGS. 3A and 3B also illustrate the leaflet 20 of the valve 10 flexing around the valve reinforcement 16. The leaflet 20 of the valve 10 can fold around the valve reinforcement 16 to accommodate the geometry of the inner lumen of the vessel wall 14 when the valve 10 is in an open state. Such folding can accommodate varying vessel wall diameters.

Figure 3C:
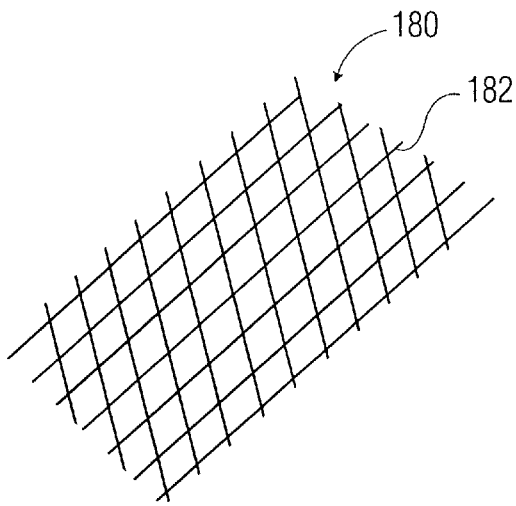
FIG. 3C illustrates a mesh of a leaflet.

In one embodiment, the leaflet 20 of the valve 10 is made of a mesh 180 having struts 182, as illustrated in FIG. 3C. The mesh 180 can be formed from a woven plastic filament material, for example. The mesh can also be formed of flexible elastic such as Nitinol, or can be formed of a biodegradable material such as Polylactid.

Figure 3D:
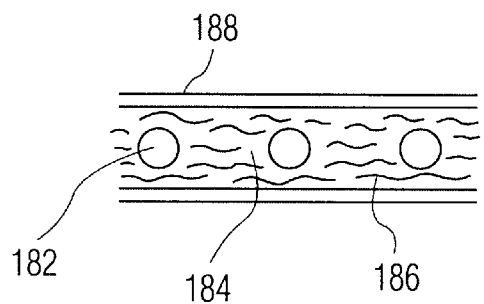
FIG. 3D illustrates tissue adhering to the struts of the mesh of FIG. 3C.

Tissue cells are used to surround the mesh 180 to form a leaflet surface. In one embodiment, prior to implanting the leaflet valve into a patient, cells are cultured on the mesh 180 to create a surface of living cells. These cells can be stem cells or endothelium cells from the recipient patent. In another embodiment, the leaflet valve is implanted into the patient without cultured cells. The openings in the mesh 180 are then closed or filled by cells which adhere to and grow on the struts 182 of the mesh 180. The cells can form an endothelium layer 188. Tissue 184 and elastic fibers 186 can fill the voids within the mesh 180, as illustrated in the enlarged view of FIG. 3D.

Figure 4:
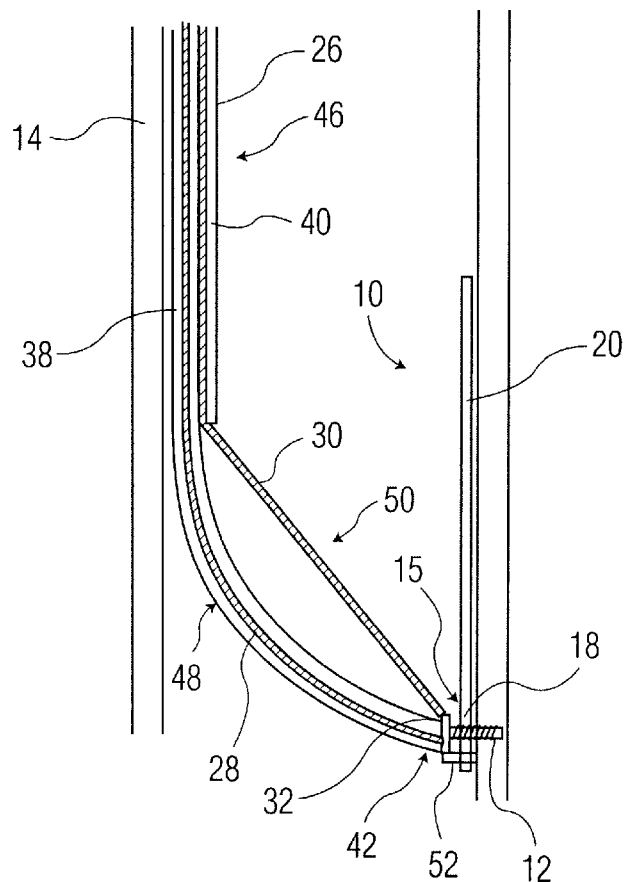
FIG. 4 shows the mounting of the valve within a vessel using an implantation device.

FIG. 4 illustrates a percutaneously implantable valve 10 being attached to the vessel wall 14. To attach the valve 10 to the vessel wall 14, an implantation device 46 can be used which can include a double lumen catheter 26, for example. The catheter 26 can include a connector driver or axle 48, for affixing the connector 12 to the vessel wall 14, and a guide 50 for adjusting the location of the driver 48. As shown, a first lumen 38 of the catheter 26, can accommodate the movement of the driver 48 which can be a flexible core 28. The flexible core 28 can be made from plastic, Nitinol, or stainless steel, for example. The flexible core 28 has sufficient axial and/or rotational stiffness so that it can be used to drive the connector 12 into the vessel wall 14. The catheter 26 can also include a catheter connector 52 to connect the valve 10 to the catheter distal tip 42 for introduction into the vessel. A release mechanism can also be included to allow the user to release the catheter from the connector after placement.

A second catheter lumen 40 can include the guide 52 which can be a cable 30. The cable 30 can be attached to the catheter tip 42 by a cable connector 32. The cable 30 can control the bending of the catheter 26 to allow placement of the valve 10 in a desired location and attachment of the valve 10 to the vessel wall 14. The cable 30 can be a flexible material. Alternatively, the cable 30 can be a stiff wire which can be used to push the catheter 26 into a straight shape. The second lumen 40 terminates at a distance of about 0.2–25 mm from the distal end 42 of the catheter to accommodate the rotational displacement of the distal end of the catheter from a first side of the lumen to the opposite side of the lumen such that the connector is oriented properly relative to the wall for insertion. For example, if the valve element has a diameter of 10 mm, the distance from the end of the second lumen to the distal end of the catheter is also about 10 mm. In the illustrated embodiment the connector must be rotated to a position where it is oriented orthogonally relative to the wall of the lumen. This may require rotation through an angle of between 70 degrees and 110 degrees.

Figure 5:
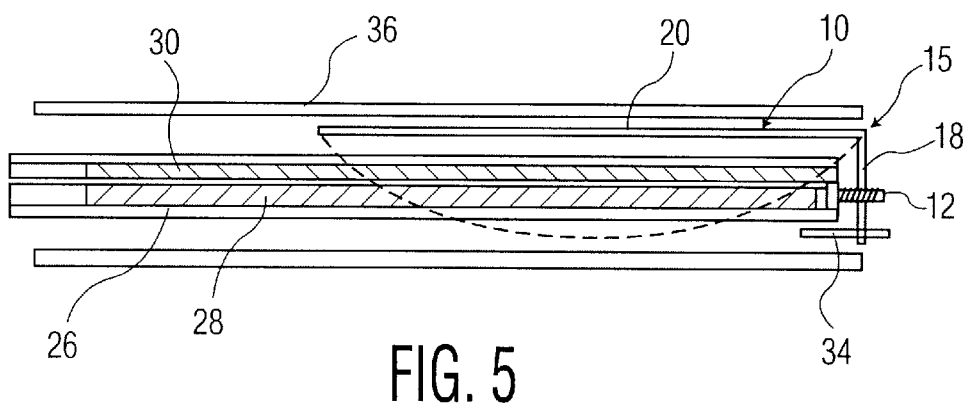
FIG. 5 illustrates the implantation device and valve within a sheath.

The implantation catheter 46 and valve 10 can be housed within a tubular sheath 36, as illustrated in FIG. 5. When placed in the sheath 36, the valve 10 can be housed within the sheath during positioning. Use of the sheath 36 provides for ease of insertion of the catheter 46 and the valve 10 through a vessel to the region of the a vessel wall 14 at which the connector is to be inserted.

Figure 6:
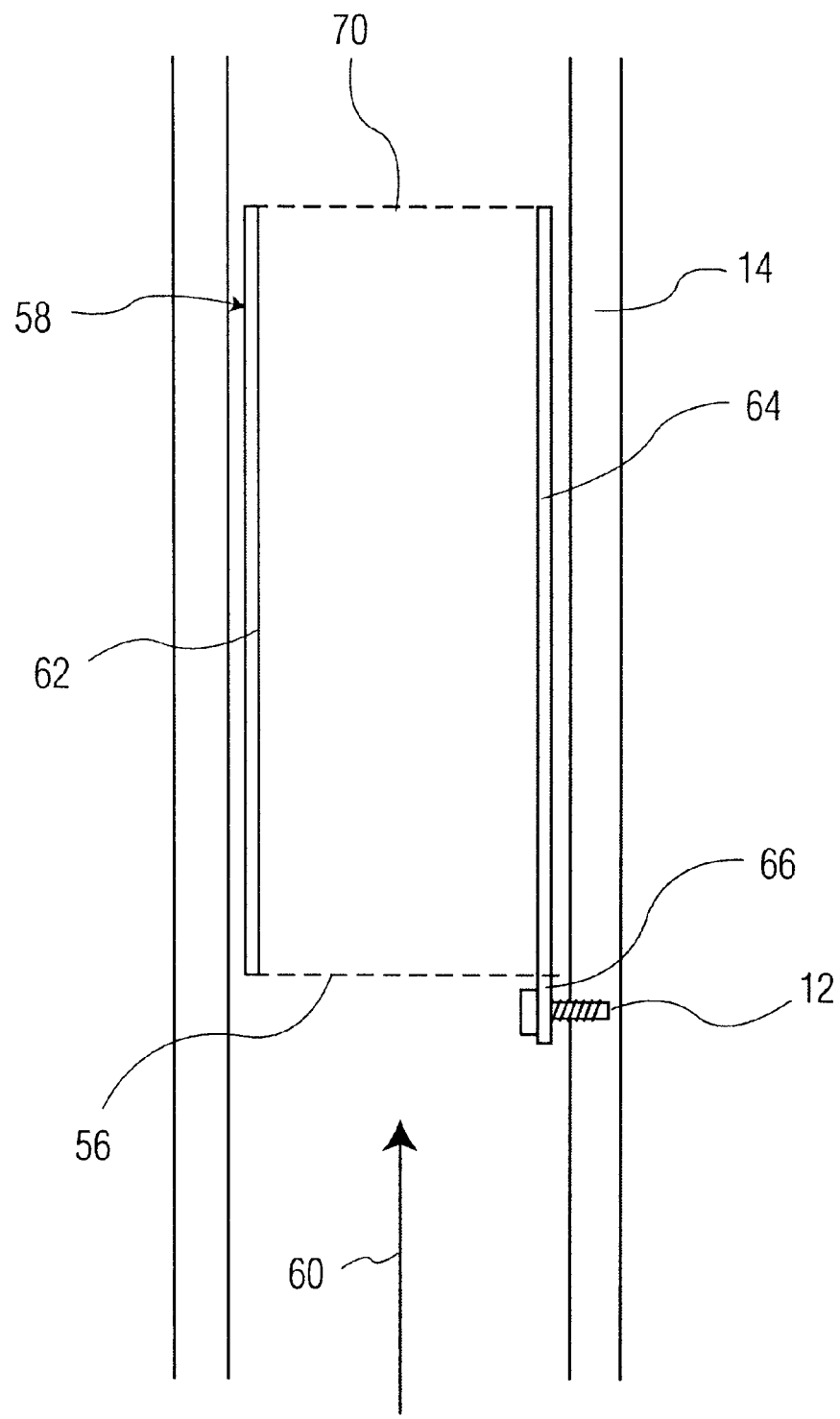
FIG. 6 illustrates a tube placed in a vessel in an open position.
Figure 7:
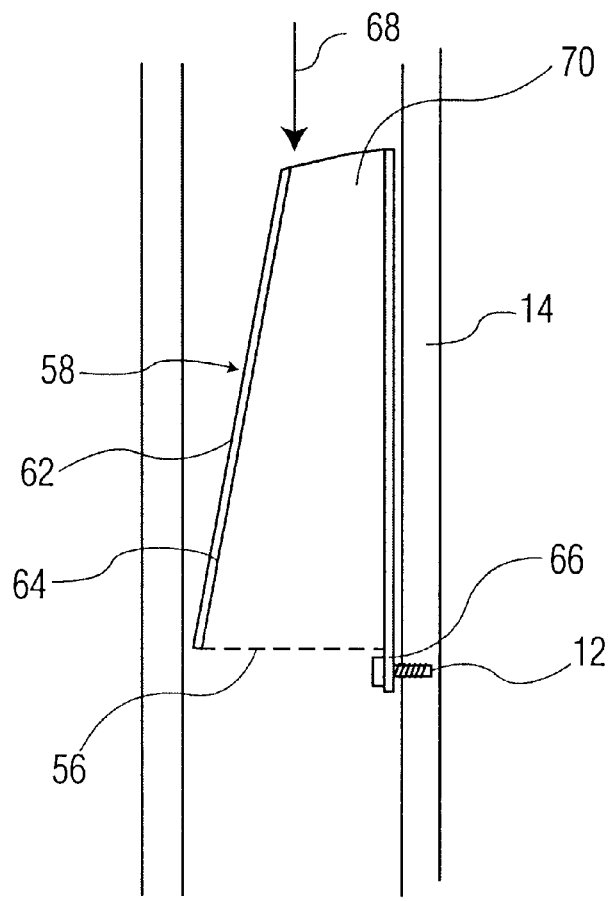
FIG. 7 illustrates a tube placed within a vessel in a closed position.
Figure 8:
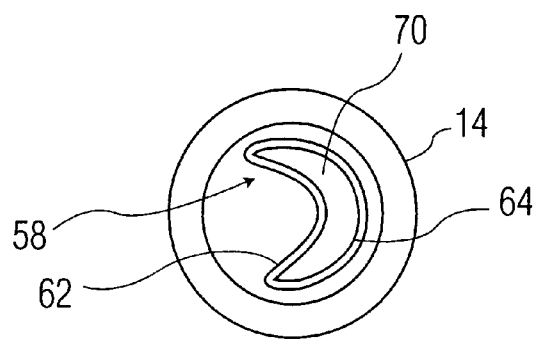
FIG. 8 illustrates a top view of the tube of FIG. 7.

An alternate valve is illustrated in FIGS. 6 through 8 and is given generally as 58. The valve 58 can be a flexible thin walled pliable tube 62. The tube 62 can be made with a silicone material. The tube 62 can be implanted coaxially into a vessel having a vessel wall 14. The tube 62 can be attached to the lumen surface region or vessel wall 14 at a base 66 by a connector or attachment mechanism 12. Preferably, the tube 62 is connected to the vessel wall 14 at a single point. The tube 62 includes a proximal opening 70 and a distal opening 56. The distal end of tub 62 can be reinforced using a frame or a thicker material, for example, to improve the stability of the attachment.

In FIG. 6, when fluid flow 60 travels from a distal source, such as during venous flow, the fluid will flow through a distal portion 56 of the tube 62. In the case of such flow, the walls 64 of the tube 62 can be separated. Such separation of the walls 64 of the tube 62 allows fluid to flow from a distal source through the proximal opening 70 in the tube.

In FIGS. 7 and 8, in the case of flow in an opposite direction 68, such as from a proximal source, the flow 68 can cause the tube 62 to collapse at its proximal end. The flow 68 then gradually collapses the tube 62 from its proximal to its distal end. Collapse of the walls 64 of the tube 62 at the proximal end of the tube 62 can cause flow interruption or reduction in this fluid flow 68. In such a case, closure of the walls 64 of the tube 62 can prevent back flow 68 of the fluid 68 towards a distal source. Collapsing of the tube 62 at its proximal end reduces the cross sectional area of the opening 70 of the tube 62, as shown in FIG. 8.

Figure 9A:
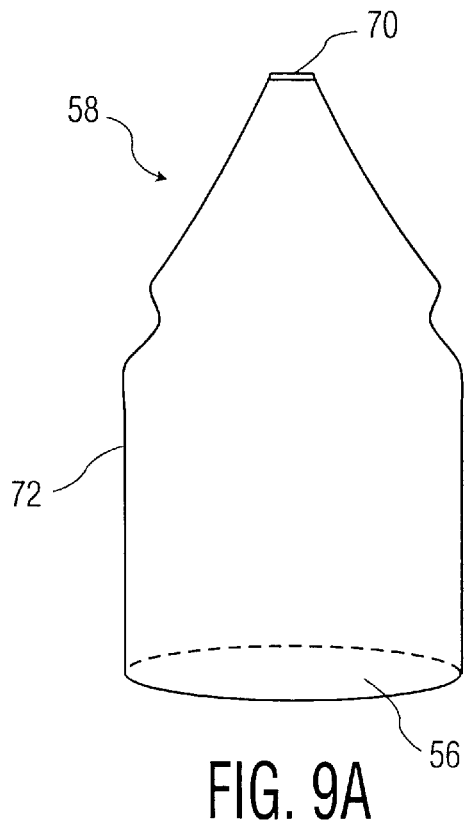
FIGS. 9A and 9B illustrate a wedge shaped tube in a side and front view, respectively.
Figure 9B:
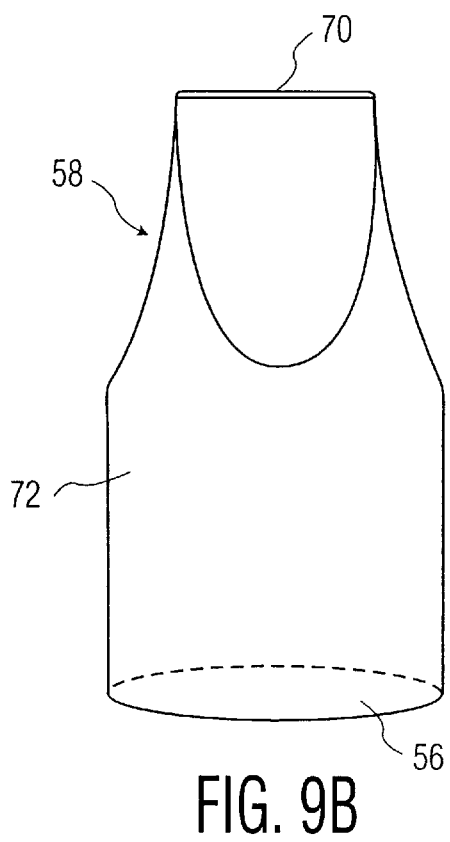

FIGS. 9A–9B and 10A–10B illustrate various configurations of the tube 62. FIGS. 9A and 9B illustrate the valve 58 as a wedge shaped tube 72. The wedge shaped tube 72 can be occluded by retrograde flow or flow from a proximal source which forces the walls 64 of the tube 72 against each other, thereby closing the tube 72.

Figure 10A:
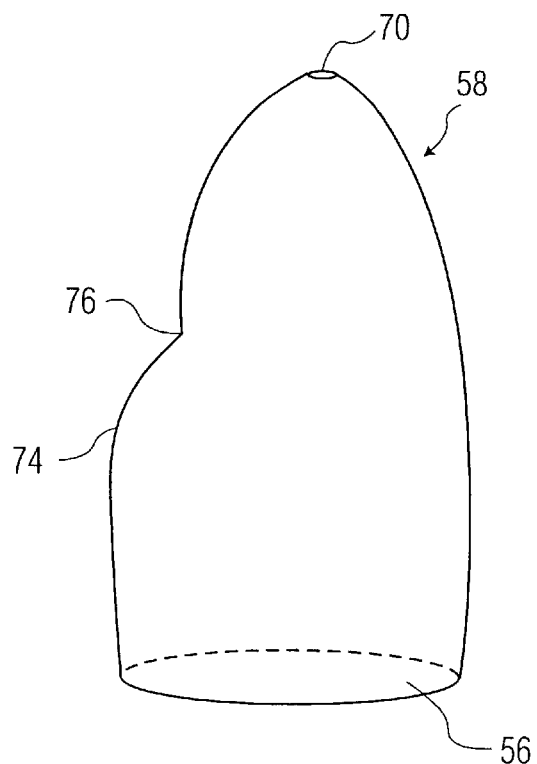
FIGS. 10A and 10B illustrate a curve shaped tube in a side view and front view, respectively.
Figure 10B:
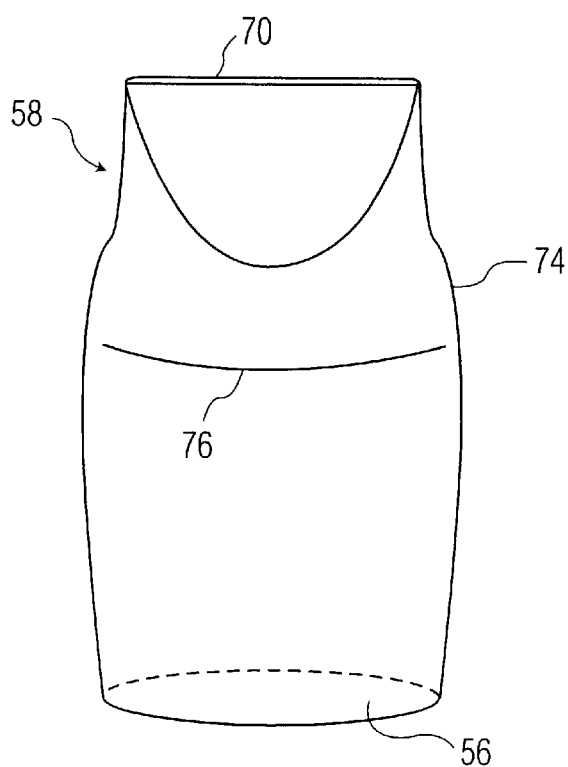

FIGS. 10A and 10B illustrates a valve 58 which is a curve shaped tube 74. The tube 74 includes a crease portion 76. The curve shaped tube 74 can prevent flow from a retrograde or a proximal source in different ways. For example, when the tube 74 is exposed to a retrograde flow, the walls of the tube 74 can close against each other, thereby closing the tube 74. Also for example, when exposed to retrograde flow, the tube 74 can tilt and kink along the crease portion 76, thereby forcing the proximal portion of the tube 74 sidewards to create an occlusion and prevent backflow.

Figure 11:
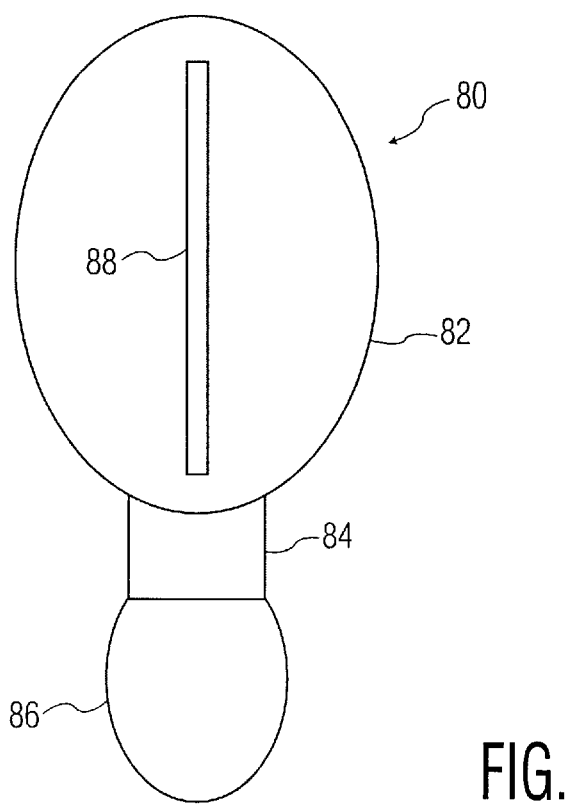
FIG. 11 illustrates a front view of a valve.
Figure 12:
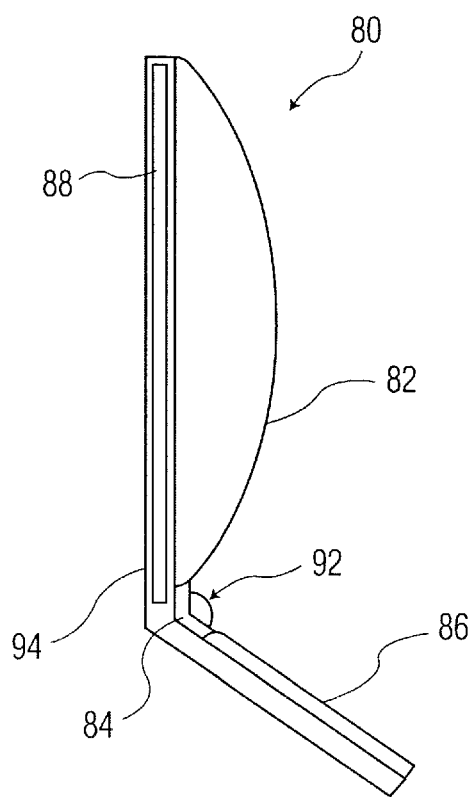
FIG. 12 illustrates a side view of a valve.
Figure 13:
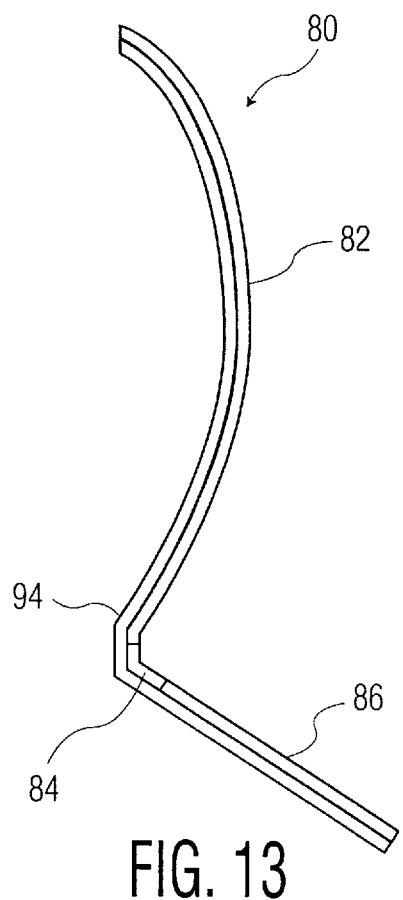
FIG. 13 illustrates an alternate embodiment of a side view of a valve.

Another alternate valve design is shown in FIGS. 11 through 13 and is given generally as 80. The valve 80 includes a leaflet 82, a hinge 84 and a base 86. The valve element 82 can be cast from a silicone material. The valve can be made from other materials described previously herein. Preferably, the valve element 82 has an oval shape. The base 86 and the valve element 82 can be connected together by the hinge 84. The hinge 84 can be made from a variety of materials. For example, the hinge 84 can be a Nitinol hinge material. The hinge 84 can also be made from a bundle of fibers, such as Kevlar™, glass or a textile, for example. Preferably, the rim of the leaflet 82 is thinner than the center portion of the leaflet 82 as illustrated in FIG. 12. The base 86 can have a size of about the size of a blood vessel. The base 86 can be attached to a lumen surface region by an attachment mechanism or connector. The leaflet 82 of the valve 80 can have a soft rim which can be silicone to increase surface contact area. It can also help to seal the valve against the vessel wall 14.

A reinforcement or frame member 88 can be imbedded into the valve to provide for stabilization. The frame member 88 can be a metal filament, for example, and can be made from a stainless steel material. The leaflet 82 and the base 86 can be connected together at an angle 92. When placed in a vessel, the angle 92 ensures that the valve 80 is closed when there is no flow within the vessel. In the area of the hinge 84, there is a thin layer of silicone to facilitate the rotation of the hinge 84. Alternatively the hinge can be used without silicone. The leaflet 82 and the base 86 can be connected with a fabric material 94 such as a woven textile. The member 88 can be mounted within the fabric 94 or the leaflet material or a combination of layers of different materials. The member 88, in combination with the fabric 94, provides stability to the valve 80 and allows the valve to be made from a thin material.

FIG. 13 illustrates an alternate embodiment of the valve shown in FIG. 11. In this embodiment, the leaflet 82 is formed in a concaved shape. With a concave shape, the edges of the leaflet 82 are thicker than the center of the leaflet 82. In such a valve 80, the valve 80 can be reinforced by a silicone rim rather than a metal rim.

The leaflet of the valve can also have a circular shape. The circular shaped valve can include a stopper. The stopper can prevent the leaflet from being moved from a proximal position to a distal position about the axis of the hinge. The stopper can be formed with or attached to either the leaflet and/or the base and prevents rotation of the leaflet relative to the base beyond a certain angle.

Figure 14:
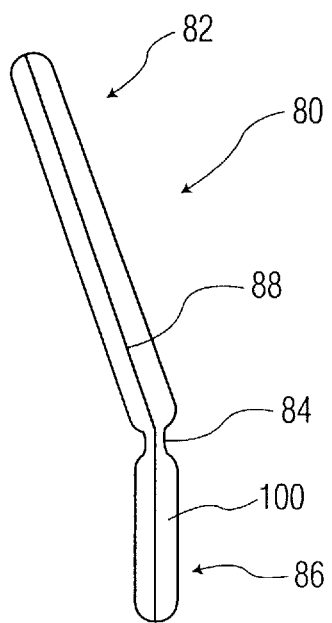
FIG. 14 shows a cross sectional view of a valve.

FIG. 14 illustrates a valve 80 having a leaf or leaflet 82 and a base 86. The leaflet 82 and the base 86 can be connected by a hinge 84. FIG. 14 shows the area of the hinge 84 between the base 86 and the leaflet 82. The leaflet 82 and the base 86 can be made from a silicone material 100. At the hinge 84, the silicone material 100 can be thinner than the silicone material on either the base 86 or the leaflet 82. The thin amount of silicone material 100 can facilitate movement of the hinge 84. The silicone 100 can be reinforced with a reinforcing material 88, located in the center of the silicone material 100. The reinforcement structure 88 can extend through the hinge 84 from the base 86 to the leaflet 82. The material properties of the reinforcing material 88 can be such that the material does not incur fatigue fractures over time. The reinforcing material can be a weaved structure, for example. The filaments of the weave structure can be very thin in order to provide a high resistance to fractures. For example, textile filaments can be used as the reinforcing material. Also, Kevlar™ can also be used as a filament material, for example. The hinge 84 can be a formed metal material in order to interconnect the base 86 with the valve 82.

FIGS. 15–24 illustrate alternate embodiments of the valve 58 shown in FIGS. 7–10. The valve, illustrated in FIGS. 15–18, is given generally as 110. The valve can include a proximal end 114 and a distal end 116. The valve 110 can be connected to a vessel wall 14 with at least one connection mechanism 12. Preferably, two connection mechanisms 12 are used to secure the valve 110 to the wall 14. The valve 110 can also include a proximal opening 118 and a distal opening 120. The valve 110 can have a valve wall 130. The thickness of the valve wall 130 can vary from the distal end 116 to the proximal end 114 such that the thickness of the wall 130 is thicker at the distal end 116 and thinner at the proximal end 114.

Figure 16:
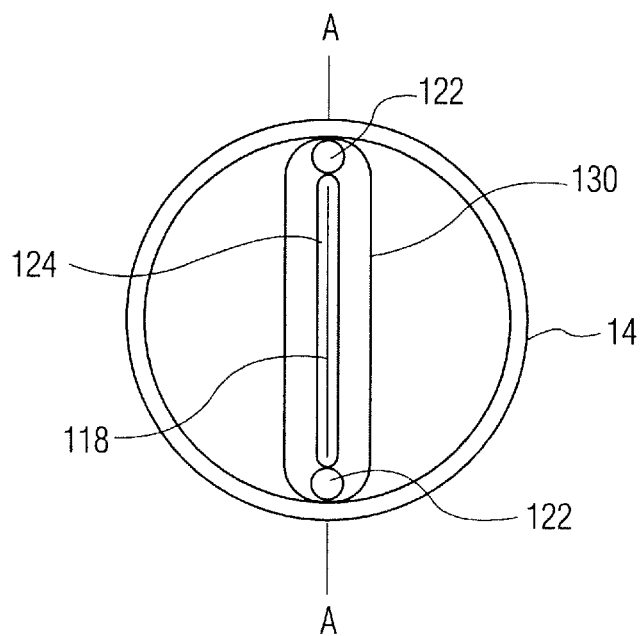
FIG. 16 illustrates a cross sectional view of the proximal end of the valve of FIG. 15.

The proximal opening 118 can be formed longitudinally in the valve 110 and can open and enlarge its cross section in the presence of flow from a distal source. FIG. 16 illustrates the proximal opening 118 of the valve 110 along line A—A in a closed position. The proximal opening 118 can include a rim 124. The rim 118 can also include a reinforcement structure 122 which can provide a constant folding of the proximal opening 118 and the reinforcement material 122. Also, the reinforcement material 122 can prevent a prolapse of the valve 110 backwards beyond the attachment 112 to the wall 114. When flow or pressure comes from a proximal direction, the proximal opening 118 and the rim 124 of the proximal opening 118 can be pressed together thus preventing backflow.

Figure 17:
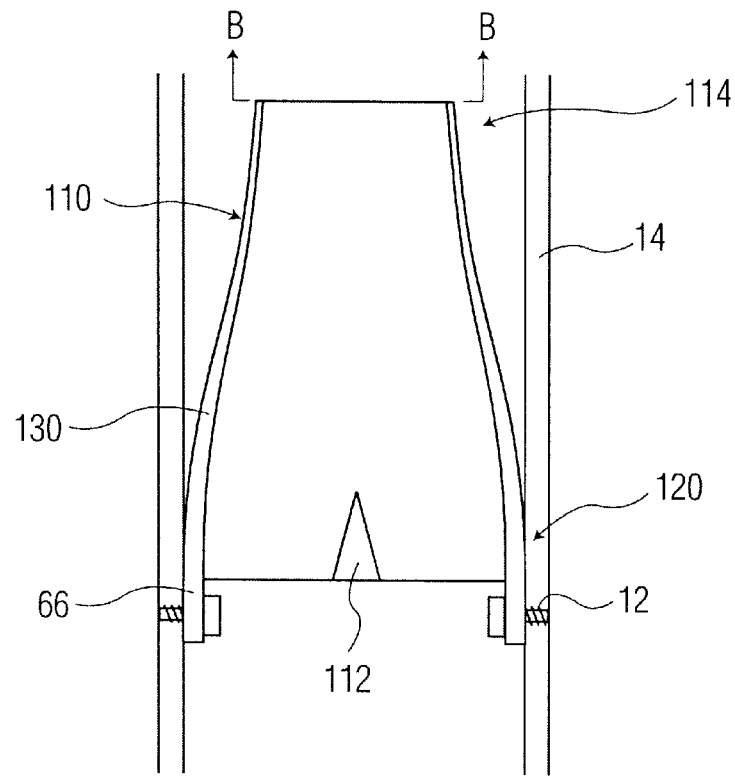
FIG. 17 illustrates a valve mounted within a vessel in an opened position.
Figure 18:
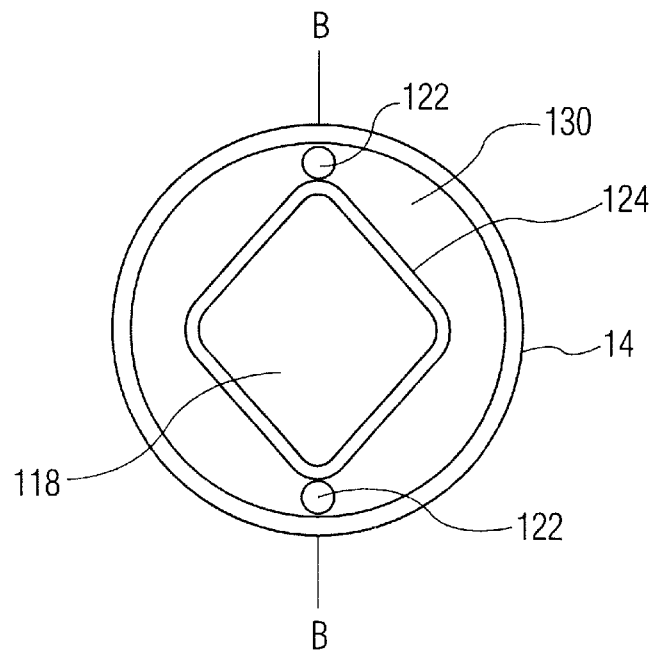
FIG. 18 shows a cross-sectional view of the proximal end of the valve of FIG. 17.

FIGS. 17 and 18 illustrate the valve 110 in an open position. FIG. 18 illustrates the opening at the valve 110 along line B—B of FIG. 17. To achieve an open position, flow from a distal source can travel through the distal end 116 and through the proximal end 116 thereby forcing open the proximal opening.

Figure 15:
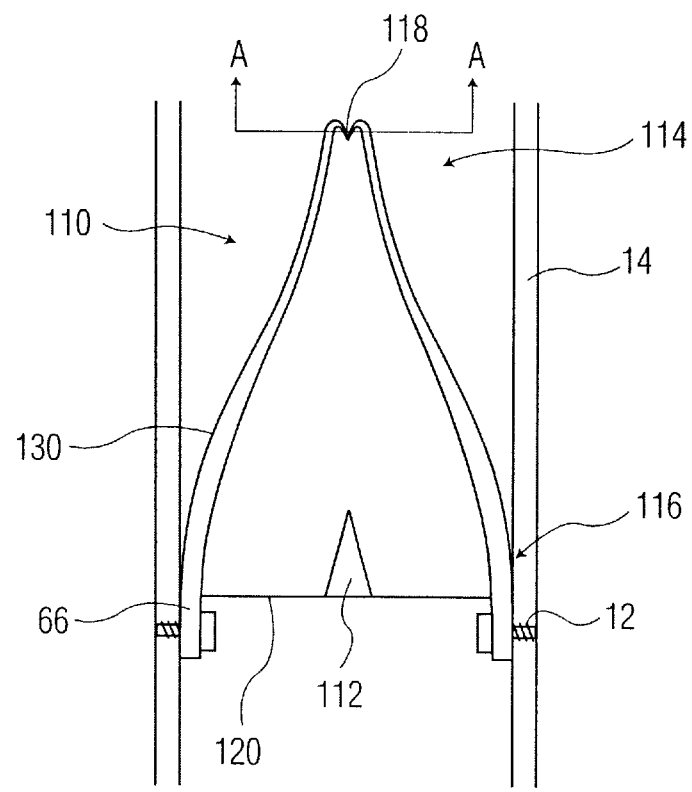
FIG. 15 shows a valve mounted within a vessel in a closed position.

As shown in FIGS. 15 and 17, the valve 110 can include a partial slit that extends longitudinally which allows for radial expansion of the valve. The slit 112 can be located at the distal end 116 of the valve 110. The diameter of the vessel wall 14 can change with pressure. Therefore, it is necessary that the wall 125 of the valve 110 be able to accommodate these changes in circumference without stressing the wall of the vessel 14. Such stressing can create thrombosis or intimal hyperplasia.

Figure 19:
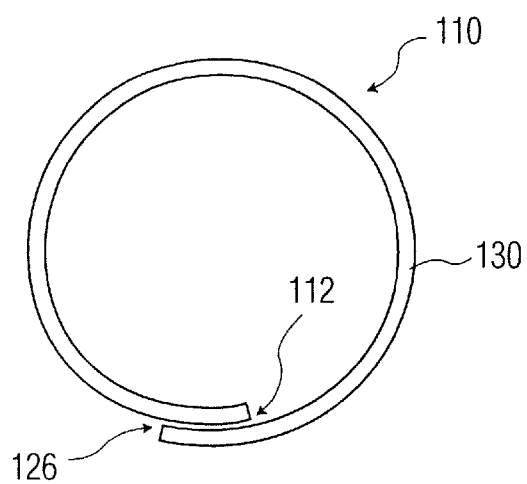
FIG. 19 illustrates a cross-sectional view of a valve having an opening mechanism.
Figure 20A:
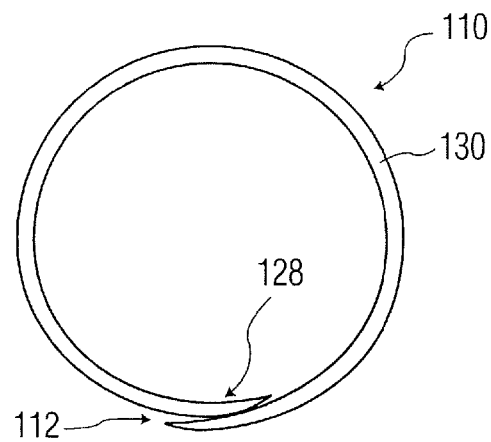
FIGS. 20A and 20B illustrate a cross sectional view of a valve having an opening mechanism in an open and a closed position, respectively.
Figure 20B:
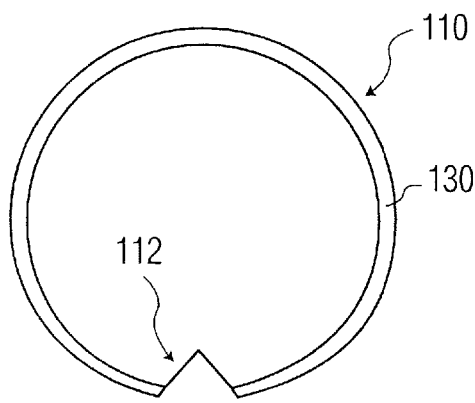

The slit or opening 112 can be axially formed. Embodiments of the opening 112 are shown in FIGS. 19, 20A and 20B. FIG. 19 illustrates a cross section of the valve 110 wherein the opening 112 is an overlapping 126 of the wall 130 of the valve 110. With the overlapping 126, the valve 110 can expand and contract in relation to the expansion and contraction of the vessel wall 14. With this overlapping 126, leakage of the venus blood through the opening 112 is reduced or eliminated. FIGS. 20A and 20B illustrate an alternate opening 112 that is a longitudinal fold 128 within the valve 110. The fold 128 allows the expansion and contraction of the wall 130 of the valve 110 during changing of diameter of the vessel wall 14. FIG. 20A illustrates the fold 128 in a closed position or a folded position. FIG. 20B illustrates the fold in an open position. The radially expanding valve of the present embodiment can also be formed using an elastic material for at least a distal portion of the valve to the connectors.

Figure 21:
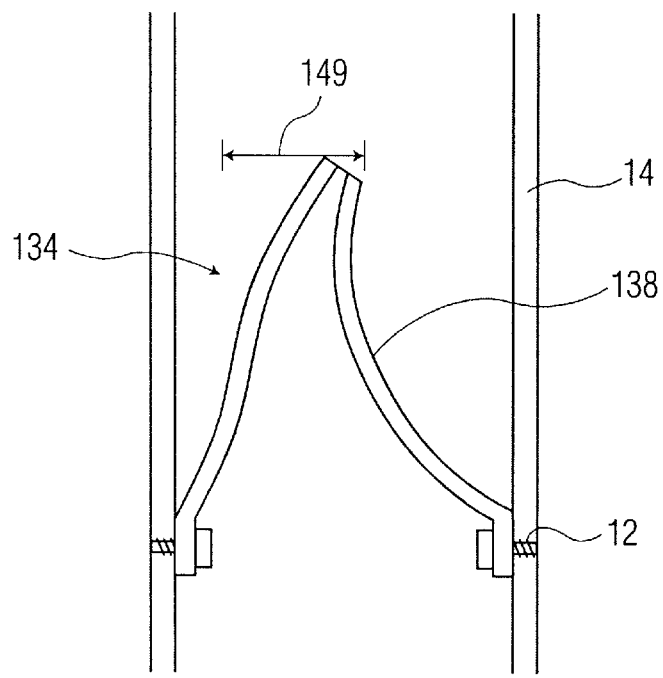
FIG. 21 illustrates a valve having a concave curved portion.
Figure 22:
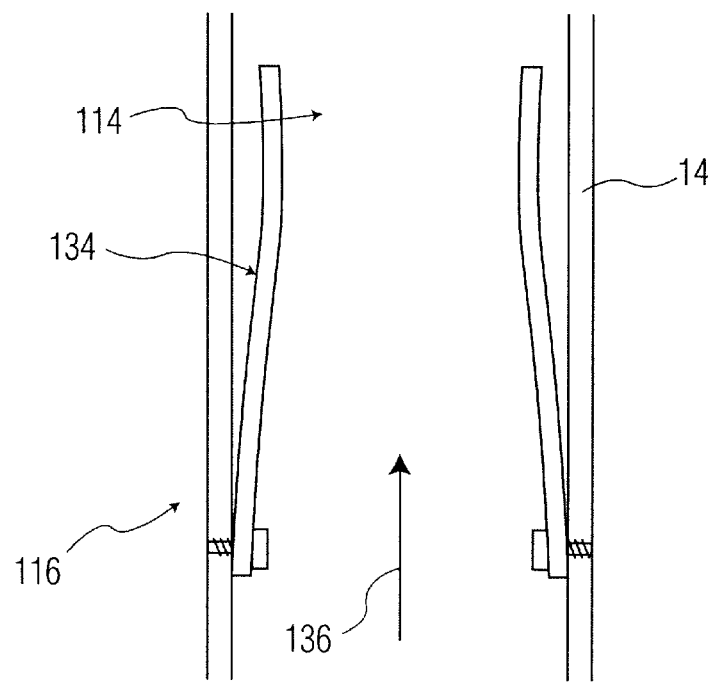
FIGS. 22 and 23 show the valve of FIG. 21 in an open position and a closed position, respectively.
Figure 23:
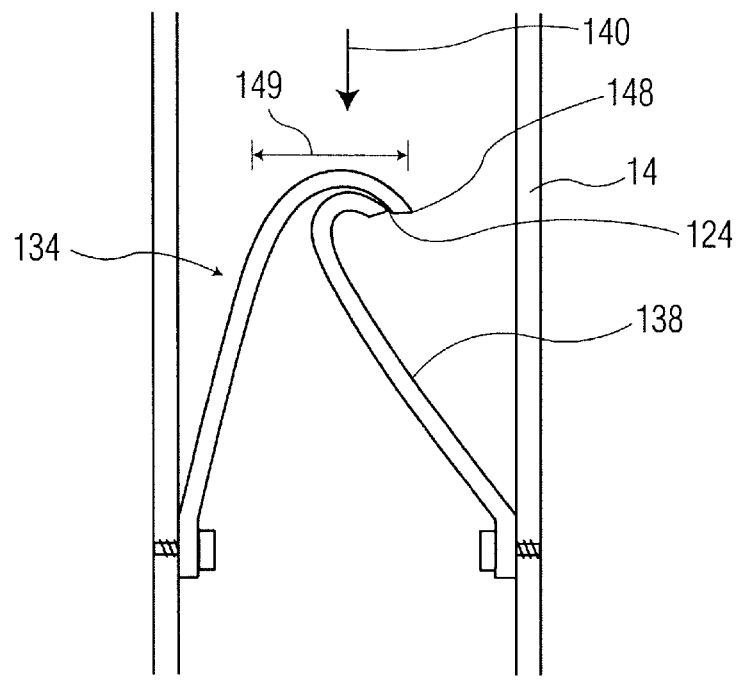

FIGS. 21–24 illustrate an alternate valve as shown in FIGS. 15–18. The valve is given generally as 134. The valve 134 can have a concave curved portion 138 and can attach to a vessel wall 14 by a plurality of connectors 12. FIG. 21 illustrates the valve 134 in the presence of no flow with no pressure gradient on the valve 134 or flow through the valve 134. FIG. 22 illustrates the valve 134 having flow 136 traveling from a distal portion 116 to a proximal portion 114. The flow 136 can force open the proximal portion 116 of the valve 134 thereby allowing fluid to flow through the valve 134. FIG. 23 illustrates the valve 134 in the presence of flow or pressure 140 coming from a proximal direction. In the presence of flow or pressure 140 from a proximal direction, the rims 148 of the valve 134 can close and align together. Also, the area of closure which can relate to the surface area of the valve 134 exposed to the flow or pressure can become larger than the area shown in FIG. 21. The area of closure is given generally as 149. With a larger area of closure 149, the flow or pressure 140 has a greater surface area to push against, thereby causing the bending of the valve 134 along the concave curved portion 138. The valve 134 can also be closed by the upper rim of the valve 134 pressing against the lower rim to provide closure of the valve 134.

Figure 24:
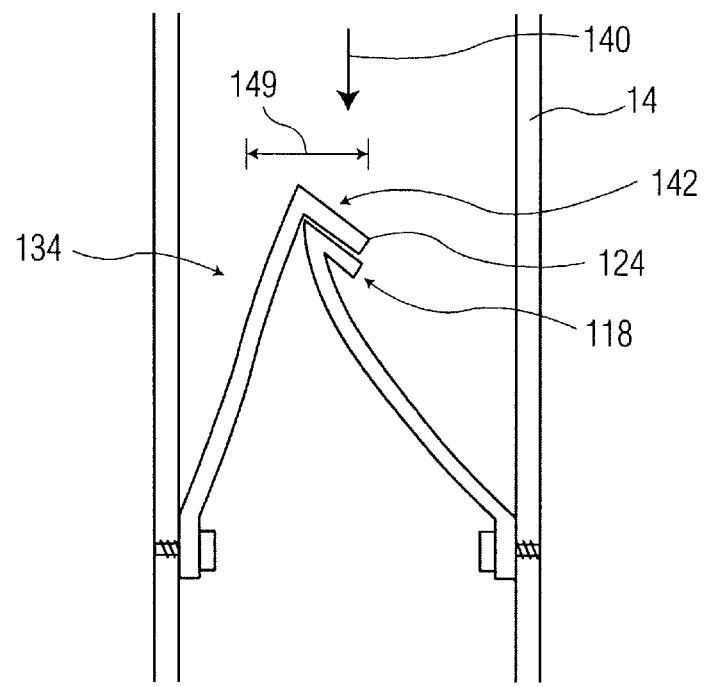
FIG. 24 illustrates an alternate valve of FIG. 21.

FIG. 24 illustrates an alternate embodiment of the valve 134 wherein the valve 134 has a kink portion 142. With an increase in proximal pressure or flow 140 relative to the valve 110, the kink portion 142 of the valve 134 can be forced to close and create a tight closure of the valve 134. The valve 134 can include a flexible material at the kink portion 142 to prevent fatigue fracture which can, in turn, destroy the valve 134. In addition to the kink portion 142, backflow can also be prevented by the rim 124 of the opening 118 of the valve 134 closing together. Backflow can also be prevented by the large area of closure 149 in this embodiment of the valve 134.

Figure 25:
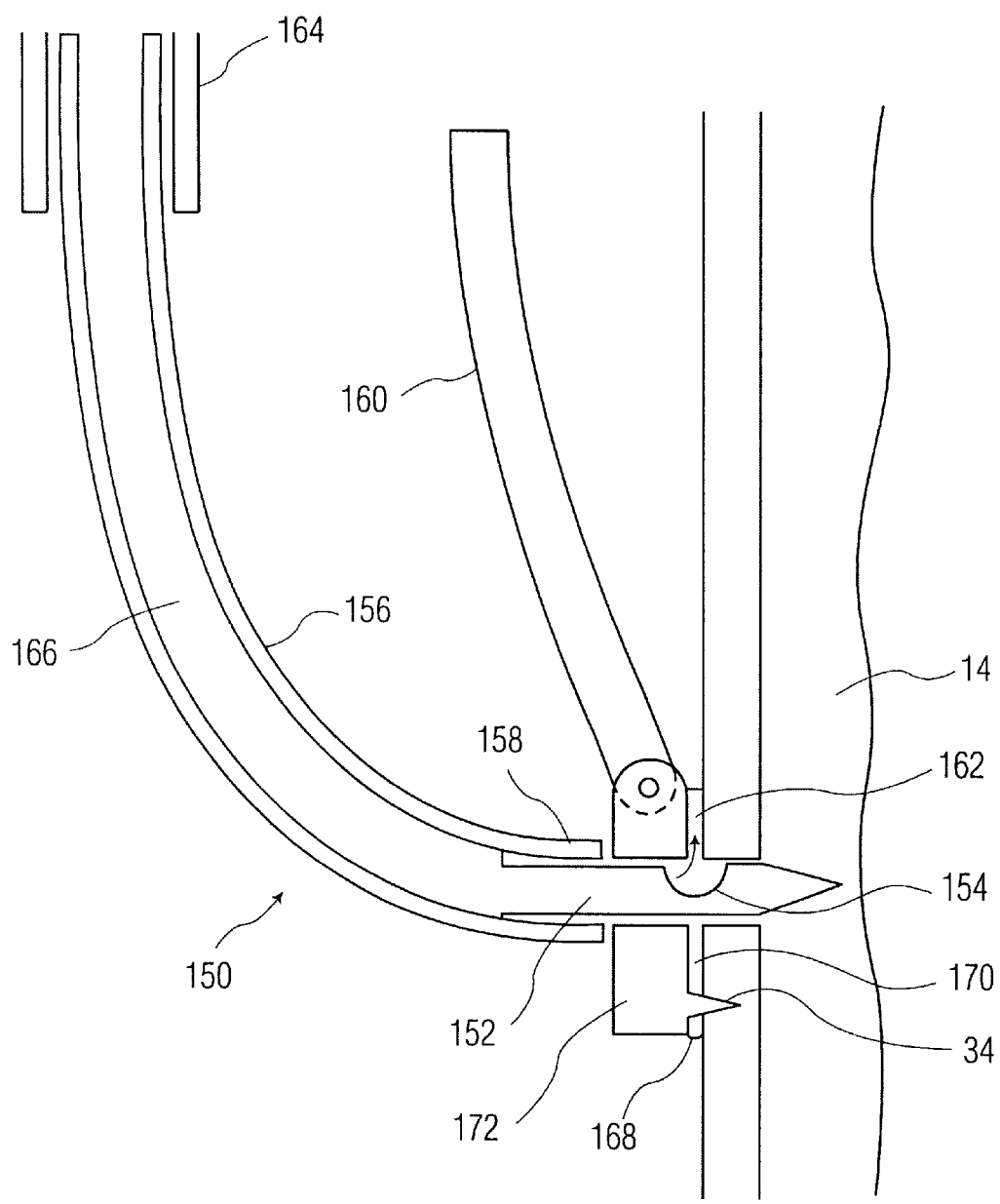
FIG. 25 shows a valve attachment mechanism.

FIG. 25 illustrates an attachment mechanism 150 for a valve 160 which can attach a valve 160 to a venous wall 14.

The attachment mechanism 150 can include a cannula 152, a catheter 156 and a sheath 164. The cannula 152 can include an aperture 154 through which a fluid can be transmitted. The cannula can be a needle and can be made from a metal material. The catheter 156 can be curved to form an arch shape. Such an arch or curve shape can allow ease of insertion of a valve element 160 into a vessel wall 14. The catheter 156 can also include a shoulder 158. The shoulder 158 can abut the base 172 during an insertion process. The shoulder can prevent the base 172 from moving during curing of an adhesive inserted at aperture 154. The catheter 156 can be introduced into a vessel wall 14 through the sheath 164. The lumen of the catheter 156 can be filled with a fluid such as a contrast material 166 which allows a user to visualize the connector 150 in a vessel wall 14 during an insertion procedure. The contrast material can give either a negative or a positive contrast during imaging. The imaging can be x-ray fluoroscopy, for example. The negative contrast material 166 can be a gas, such as carbon dioxide. A positive contrast medium can preferably be a non-ionic contrast medium. The lumen of the catheter 156 can also be used to introduce a fluid such as an adhesive to secure the base 172 to the wall 14 and can include a fluid such as a glucose solution which can force the adhesive through the catheter 156.

To insert a valve in a vessel wall 14, the valve 150 can be mounted to the end of the pre-bent catheter 156. The valve 150 can be mounted around the cannula 152. The base 172 of the valve can be mounted over the cannula 152 to the catheter and can be secured by the shoulder 158.

To attach the valve 160 to a venous wall 14, the wall 14 can be punctured by the tip of the cannula 152. The base 172 of the valve 160 can include a secondary connector or attachment mechanism 34 to help secure the valve 160 to the wall 14. The base 172 can also form a chamber 170 between the base 172 and the vessel wall 12. The base 172 can include a rim 168 which can prevent spilling of the adhesive into the lumen of the vessel. The lumen of the catheter 156 can then be filled with a negative or positive contrasting material 166. After having filled the lumen of the catheter, a small amount of adhesive material 162 can be introduced in the catheter. This amount of adhesive material 162 corresponds to the volume of a chamber 170 to prevent spilling of flue into the circulatory system and the possibility of a resulting embolism. The adhesive can also be mixed with a contrast medicine such as Lipidol (an only iodine contrast medicine). Other biocompatible glues such as Histocryl can be used. After the adhesive 162 volume has been introduced, another fluid can be injected into the catheter 156 such as a highly concentrated glucose solution or a contrast medium which does not introduce curing of the adhesive in the catheter 156. The adhesive can leave the catheter system through the aperture 154 of the cannula 152. The aperture 154 can be arranged at a distance from the catheter shoulder 158 in such a manner that the aperture 154 can be in the chamber 170 below the base 172 of the valve 160 and between the base 172 of the valve 160 and the arterial or venous wall 14. After curing of the adhesive, the catheter 156 with the cannula 152 can be pulled outward leaving the valve 160 secured to the vessel wall 14.

As an alternate to using a cannula, a metal tube can be introduced through the catheter 156. The metal tube can include a closed tip and an aperture 154. The metal tube can have a stopper to adjust the position of the aperture 154 to the position where the adhesive material (eg. Nitional™) has to be delivered. The metal tube can consist of a nickel titanium material and can be bendable. The tube can be used for other purposes also, such as to adjust dissections after angioplasty to the base of the vessel wall while gluing.

The distance between the aperture of the metal tube and the end of catheter can be longer, thus allowing injection of drugs into the perivascular tissue for the prevention of intimal hyperplasia. After injection of the drug, the puncture hole can be closed with a small amount of adhesive to inhibit perivascular bleeding and back leakage of drug into the vessel lumen.

Alternately, the base 172 of the valve 160 can include a self adhesive to secure the base 172 to the vessel wall 14. The valve 160 can be delivered to an attachment site using an attachment mechanism. The valve 160 can then be secured to the vessel wall 14 by contacting the self adhesive with the wall 14. After curing of the self adhesive, the attachment mechanism can be removed from the attachment site.

While this invention has been particularly shown and described with references to preferred embodiments thereof, it will be understood by those skilled in the art that various changes in form and details may be made therein without departing from the scope of the invention encompassed by the appended claims.

What is claimed is:

1. A body lumen valve comprising:
   a base;
   a valve element comprising tissue disposed on a mesh, said valve element connected to the base such that the valve moves relative to the base between an open position and a closed position; and
   a connector that attaches the base directly to a body lumen surface region.

2. The valve of claim 1 wherein the valve element comprises a rim formed of a flexible material.

3. The valve of claim 1 wherein the valve element comprises at least one valve.

4. The valve of claim 1 wherein the valve further comprises a second connector.

5. The valve of claim 1 wherein the connector comprises a pin, a screw or a staple.

6. The valve of claim 1 wherein the valve element further comprises a leaflet attached to a frame.

7. The valve of claim 1 wherein the valve element and the base comprise a unitary structure having a hinge such that the valve element rotates relative to the base at the hinge.

8. The valve of claim 1 wherein the valve element comprises a substantially circular member having a soft peripheral rim.

9. The valve of claim 1 wherein the valve element has a thickness in a range between 0.2 mm and 3.0 mm, and a diameter in a range between 2 mm and 25 mm.

10. The valve of claim 1, wherein said tissue is cultured onto the valve element prior to implantation into a surgical site.

11. The valve of claim 1 wherein said tissue is adhered to the mesh after implantation into a surgical site.

12. A valve comprising:
   a base;
   a connector that attaches the base directly to a body lumen surface region; and
   a tubular wall attached to the base, the tubular wall formed of a silicone material and having a distal end with a distal opening and a proximal end with a proximal opening such that fluid flow from the distal end to the proximal end forces the tubular wall into an open position and fluid flow from the proximal end to the distal end forces the tubular wall into a closed position.

13. The valve of claim 12 wherein the proximal opening comprises a rim.

14. The valve of claim 12 wherein the proximal opening comprises at least one reinforcement member.

15. The valve of claim 12 wherein the valve comprises a radially expanding region.

16. The valve of claim 15 wherein the radially expanding region comprises an overlapping portion.

17. The valve of claim 15 wherein the radially expanding region comprises a longitudinal fold.

18. The valve of claim 12 wherein the valve further comprises a concave curved portion.

19. An implantable venous valve comprising:
   a base;
   a connector that attaches the base directly to a body lumen surface region;
   a leaflet comprising a rim and a center portion, the rim being thinner than the center portion; and
   a hinge connecting the base to the leaflet such that the leaflet moves relative to the base between an open position and a closed position.

20. The valve of claim 19 wherein the leaflet comprises an oval shape.

21. The valve of claim 19 wherein the leaflet comprises a concave shape.

22. The valve of claim 19 wherein the valve comprises a frame.

23. The valve of claim 22 wherein the frame comprises a metal filament.

24. The valve of claim 19 wherein the valve is formed of a silicone material.

25. The valve of claim 19 wherein the valve further has a fabric material connecting the leaflet and the base.

26. The valve of claim 19 wherein a frame is located between a first layer and a second layer of the leaflet.

27. The valve of claim 19 wherein the leaflet comprises a mesh.

28. The valve of claim 27 wherein the mesh comprises a surface formed of cells.

29. The valve of claim 28 wherein the cells are cultured onto the mesh.

30. The valve of claim 28 wherein the cells adhere to the mesh after implantation into a surgical site.

31. An implantable venous valve comprising:
   a base;
   a connector that attached the base to a lumen surface region;
   a leaflet; and
   a hinge connecting the base to the leaflet such that the leaflet moves relative to the base between an open position and a closed position, wherein said valve is formed of a silicone material.

32. The valve of claim 31 wherein the leaflet comprises an oval shape.

33. The valve of claim 31 wherein the leaflet comprises a rim and a center portion, the rim being thinner than the center portion.

34. The valve of claim 31 wherein the leaflet comprises a concave shape.

35. The valve of claim 31 wherein the valve comprises a frame.

36. The valve of claim 35 wherein the frame comprises a metal filament.

37. The valve of claim 31 wherein the valve further has a fabric material connecting the leaflet and the base.

38. The valve of claim 31 wherein a frame is located between a first layer and a second layer of the leaflet.

39. The valve of claim 31 wherein the leaflet comprises a mesh.

40. The valve of claim 39 wherein the mesh comprises a surface formed of cells.

41. The valve of claim 40 wherein the cells are cultured onto the mesh.

42. The valve of claim 40 wherein the cells adhere to the mesh after implantation into a surgical site.

* * * * *